United States Patent [19]

Eckels

[11] 4,326,541
[45] Apr. 27, 1982

[54] BLOOD SAMPLE TAKING DEVICE
[75] Inventor: John F. Eckels, Simi, Calif.
[73] Assignee: Arnold M. Heyman, Burbank, Calif.
[21] Appl. No.: 132,830
[22] Filed: Mar. 24, 1980
[51] Int. Cl.$^3$ ............................................. A61B 5/14
[52] U.S. Cl. ................................ 128/766; 128/764; 128/274; 251/334; 251/321; 251/DIG. 4
[58] Field of Search ............. 128/764, 766, 768, 763, 128/274; 251/334, 320, 321, DIG. 4

[56] References Cited

U.S. PATENT DOCUMENTS

| 1,930,040 | 10/1933 | Crowley | 137/DIG. 4 |
|---|---|---|---|
| 2,832,344 | 4/1958 | Davidson | 128/766 |
| 3,143,109 | 8/1964 | Gewertz | 128/766 |
| 3,304,934 | 2/1967 | Bautista | 128/764 |
| 3,308,809 | 3/1967 | Cohen | 128/766 |
| 3,577,980 | 5/1971 | Cohen | 128/766 |
| 3,584,834 | 6/1971 | Reid et al. | 137/DIG. 4 |
| 3,848,579 | 11/1974 | Villa-Real | 128/764 |
| 4,073,288 | 2/1978 | Chapman | 128/766 |
| 4,166,450 | 9/1979 | Abramson | 128/764 |
| 4,215,702 | 8/1980 | Ayer | 128/766 |

FOREIGN PATENT DOCUMENTS

| 2750454 | 5/1979 | Fed. Rep. of Germany | 128/764 |
|---|---|---|---|
| 1586087 | 12/1969 | France | 128/766 |
| 464109 | 6/1951 | Italy . | |
| 469055 | 2/1952 | Italy | 128/766 |

Primary Examiner—Kyle L. Howell

[57] ABSTRACT

An improved blood sampling device particularly suited for obtaining arterial blood samples. The device includes a molded plastic carrier having front and rear needles and a valve for controlling flow between the needles. The rear needle punctures the stopper of an evacuated sampling tube when it is inserted into the carrier. The front needle is then inserted into the patient and the value, which may be a one piece device made of a resilient material such as polyurethane, is opened to allow blood to be drawn into the sampling tube.

4 Claims, 4 Drawing Figures

U.S. Patent     Apr. 27, 1982     4,326,541
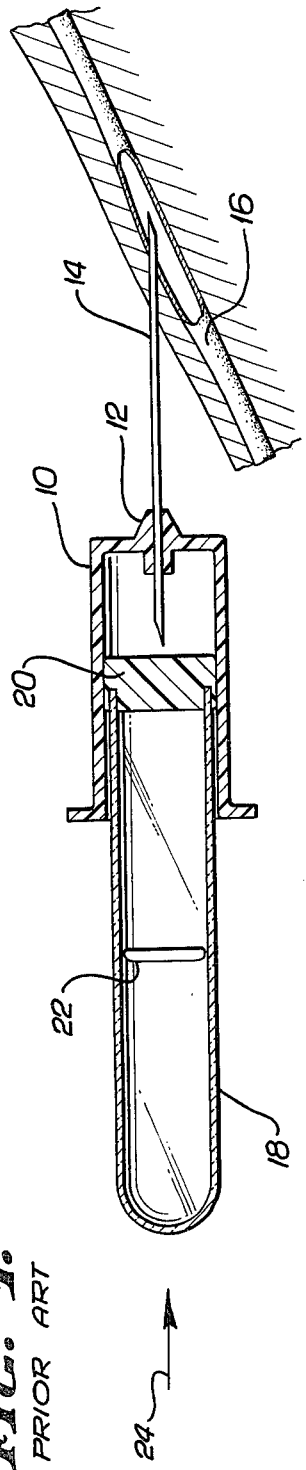
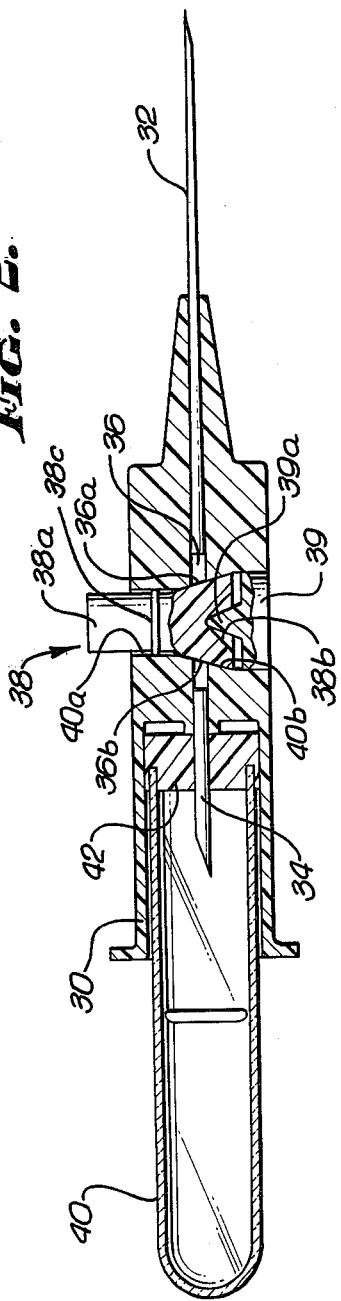
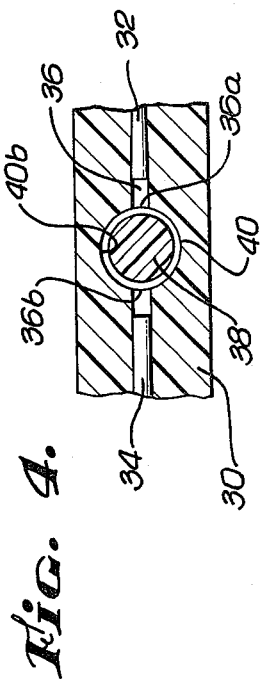

BLOOD SAMPLE TAKING DEVICE

BACKGROUND OF THE INVENTION

1. Field of the Invention

This invention relates to a system which collects a specific volume of arterial or venous blood for gas analysis or standard laboratory tests.

2. Description of the Prior Art

Presently, the most widely used arterial blood gas sampling technique employs a low resistance plunger type syringe which is heparinized prior to use in order to prevent blood clotting. The syringe is heparinized by drawing liquid heparin into it. The volume of liquid heparin necessary to adequately heparinize the syringe can cause inaccuracies in the gas analysis of the blood. For example, the heparin can introduce a change in the order of 6% to 24% in the measurement of the gas $PCO_2$, depending primarily upon the volume of heparin which is actually used. Similarly, inaccuracies on the order of 2% to 6% in the measurement of $PO_2$ gas levels may also be introduced when a plunger type heparinized syringe is used.

In order to overcome the problems of sample contamination caused by the use of a plunger type liquid heparinized syringe, a vacuum tube has been developed which contains a dry lyophilized heparin disc. The vacuum tube includes a seal providing stopper at one end through which a needle can be inserted. When the vacuum seal is broken, the heparin disc breaks up and coats the interior of the vacuum tube.

In general, a needle is inserted into a patient's vein or artery and a vacuum tube is then inserted over the rear end of the needle, thus breaking the vacuum seal and drawing blood into the vacuum tube. The needle and tube are usually carried within a holder and the stopper is held within the holder by means of a friction fit. Since the tip of the needle is already in the artery or vein when the vacuum tube is activated (i.e., when the vacuum seal is broken and the tube forced into flow communication with the needle), the activation must be accomplished carefully in order to prevent undesirable transection or pulling out of the blood vessel. When a vessel is transected, blood leakage into the surrounding tissue may cause a hematoma.

A further problem with the typical vacuum tube system is that it is a two step process which requires the technician to reposition his hands during sample collection. The technician uses one hand to stabilize and localize the blood vessel during insertion of the needle. After the needle is inserted, the technician must use that hand to apply the required force for activation of the vacuum tube. This removes the technician's ability to maintain the required stabilization and localization of the vessel, thus increasing the possibility of transection or pulling out.

Thus the major drawback of the above described system is that a longitudinal force, i.e., a force along the axis of the needle and vacuum tube, must be applied in order to activate the tube. This longitudinal force is generally perpendicular to the direction of the blood vessel and a slight movement can thus cause transection of the vessel. In order to overcome this problem, devices have been developed which include a valve which is actuated by the application of lateral rather than longitudinal forces. Devices of this type are disclosed in U.S. Pat. Nos. 3,143,109 to Gewertz, 3,308,809 to Cohen, Italian Pat. No. 469,055 and Italian Pat. No. 464,109. With the exception of Gewertz, all of these patents disclose unitary structures. Thus, they cannot be used with a separate vacuum tube. In one embodiment of Gewertz, the valve and tube arrangement is unitary and the needle section is detachable. This type of embodiment could not be used to obtain arterial blood samples, since the arterial pressure would force blood through the needle prior to the attachment of the valve and tube assembly. In a second embodiment of Gewertz, an integral needle and valve arrangement is provided having a cylindrical upper body portion having corrugated ridges for engaging receptacles, bottles or the like. This type of device can not be utilized with the typical vacuum tube having a rubber sealing stopper at one end since it does not contain any means of breaking the vacuum seal.

SUMMARY OF THE INVENTION

The present device is directed to a blood sampling device which includes a combination of features not provided by any of the prior art devices. The blood sampling device is designed to be used in conjunction with vacuum tubes having a rubber sealing stopper and including a predetermined amount of lyophilized heparin therein. This type of vacuum tube is in widespread use in the medical industry, and the blood sampling device of the present invention does not require the use of a specially designed vacuum tube. The device includes a carrier which has a forward puncture needle which is inserted into a blood vessel and a rear puncture needle which is used to break the vacuum seal of the vacuum tube. The needles are in flow communication with one another, and a valve is included between them to control the flow of blood therethrough. In operation, the valve is initially closed and a vacuum tube is inserted into the carrier such that the rear needle breaks the vacuum seal. Because the valve is closed, however, the vacuum conditions will remain. The forward needle is then inserted into the patient's blood vessel by a technician or nurse. The valve is then opened by the application of a force which is generally perpendicular to the axes of the needles and vacuum tube. The application of this lateral rather than longitudinal force minimizes the tendency of the forward needle to either transect the vessel or be withdrawn from the vessel.

An extremely beneficial feature of the above design is that it allows the technician or nurse to obtain a blood sample without having to reposition his hand. One hand is used to localize and stabilize the blood vessel so that the forward needle can be inserted cleanly into the vessel, the other hand is used to grasp the carrier. After the needle has been inserted into the patient the technician simply squeezes the valve with the hand already on the carrier to permit blood to flow into the vacuum tube. This is in sharp contrast to the system which is in typical use, where the technician must remove the hand which is used to stabilize the vessel and use it to activate the vacuum tube.

Unlike prior designs which incorporate a valve arrangement, the present invention includes a replaceable tube and a system which can be used to obtain arterial as well as venous blood samples. If more than one sample is required, the valve is closed and the first vacuum tube removed and replaced by a second vacuum tube. The closing of the valve prevents arterial blood pressure from forcing blood through the needles.

BRIEF DESCRIPTION OF THE DRAWINGS

In the drawings:

FIG. 1 is a side plan view of a prior art blood sampling device;

FIG. 2 is a side plan view of the blood sampling device of the present invention;

FIG. 3 is a plan view showing details of the operation of the valve included in the present invention; and FIG. 4 is a top section view of the valve taken along lines 4—4 of FIG. 3.

DESCRIPTION OF THE PREFERRED EMBODIMENT

Referring to FIG. 1, a typical prior art blood sampling device is shown. The sampling device includes an open ended tubular carrier 10 having a collar 12 through which a needle 14 passes. The front end of the needle 14 is shown positioned in a blood vessel 16 of a patient. The rear end of the needle 14 extends into the interior of the carrier 10. A vacuum tube 18 is shown inserted within the carrier 10. The vacuum tube 18 has a rubber stopper and seal 20 positioned over the end of the tube 18 which fits into the carrier 10. The diameter of the stopper 20 is slightly larger than that of the vacuum tube 18 and is held within the inside of the carrier 10 by means of a friction fit. The vacuum tube 18 includes a disc of lyophilized heparin 22 within its interior.

In the configuration shown in FIG. 1, the needle 14 has already been inserted into the vessel 16 but a blood sample has not yet been taken. In order to obtain a sample, the vacuum tube 18 must be pushed forward in the direction of arrow 24. This causes the rear end of the needle 14 to pierce the stopper 20, thus causing the vacuum within the tube 18 to draw blood into the tube via the needle 14. It can be seen that the force needed to activate the vacuum tube is directed along the axis of the needle 14 and generally perpendicular to the vessel 16. In addition, in order to push the tube 18 in the direction of arrow 24, the technician must hold the carrier 10 with one hand and use the other hand to activate the tube 18. The combination of force application along the longitudinal axis of the needle 14 and the relatively awkward method of activation increases the possibility of transection of the vessel 16 by the needle 14 or withdrawal of the needle 14 from the vessel 16.

Referring now to FIGS. 2, 3 and 4, the blood sampling device of the present invention incorporates a valve arrangement which permits the obtaining of a blood sample by the application of a force perpendicular to the longitudinal axis of the needle rather than in the direction of the axis. The sampling device includes a molded plastic carrier 30 having a central passage way 36. Secured within the passageway is a forward needle 32 and a rear needle 34. An integral eleastic valve 38 seals off the passageway 36 between the forward needle 32 and rear needle 34. The needles 32 and 34 may be made detachable if desired. The valve 38 is shaped to fit within an opening 40 that includes a generally cylindrical portion 40a connected to a lower frusto-conical portion 40b, and has a generally conical indentation 38b integrally formed on its bottom surface. The valve 38 also includes an upper activation button 38a and a sealing ridge 38c. The passageway 36 intersects the lower portion 40b, and when the valve 38 is in the position shown in FIG. 2, its surface contacts and seals the points 36a and 36b where the passageway 36 intersects the opening 40b.

Located beneath the valve 38 is a non-removable plug 39 which includes an upwardly extending conical portion 39a. The portion 39a applies pressure to the bottom of the valve 38 so as to force the sides of the valve upward and outward to seal the passageway 36. The valve 38 is made of a resilient material such as polyurethane. In the present embodiment of the invention, an injection moldable material sold by Shell under the trademark Kraton is utilized to make the valve 38.

To operate the blood sampling device of FIG. 2, a vacuum tube 40 which includes a stopper 42 is inserted into to the carrier 30 such that stopper 32 is pierced by the rear needle 34. Because the valve 38 is closed, the vacuum condition of the tube 40 remains intact. The forward needle 32 is then inserted into a vein or artery of a patient. The valve button 38a is then pressed in a direction indicated by an arrow 44. This forces the valve 38 to be compressed downward and around the conical portion 39a and moves the valve wall away from contact with the openings 36a and 36b as shown in FIG. 3. This allows blood to flow from the vessel through the forward needle 32, around the valve 38 and through the rear needle 34 into the vacuum tube 40. The pressing of the valve 38 causes the vacuum force of the tube 40 to draw on blood from the blood vessel into the tube 40. The cylindrical portion of the valve 38 can be made relatively stiff in order to increase the compressive force on the frusto-conical portion.

Since the valve 38 and forward needle 32 are contained in a single device, no problems are presented with respect to the sampling of arterial blood. That is, at no time when the forward needle is located within an artery will there be an open communication between the needle 32 and the outside atmosphere. Thus, arterial blood pressure cannot force blood out of the needle 32.

Although only a single valve arrangement has been described, it is clear that many different valve configurations could be successfully utilized. However, the carrier is designed as a disposable device and low cost is thus of paramount importance. The inherent simplicity of the valve arrangement which has been described enables the device to be manufactured at an extremely low cost. The adapter can include as few as 4 components (a carrier, forward and rear needles and a valve). Therefore, although other more complex valve and carrier arrangements could be used, the configuration shown provides unique advantages.

In summary, the present invention is directed to a blood sampling adapter which is designed to be used in conjunction with a vacuum tube which is sealed by means of a stopper located at one end and which is designed to have its vacuum field broken by the piercing of the stopper. The adapter comprises a carrier made of plastic or similar material which includes a central passageway having a forward needle and a rear needle retained therein and a valve located within the carrier and operable to close and open the passageway to provide a flow communication from the front needle to the rear needle. The carrier includes a vacuum tube holding portion into which the rear needle extends. When a vacuum tube is inserted into the holding portion, the rear needle pierces the stopper, thus placing the rear needle in communication with the vacuum. The forward needle is then inserted into a blood vessel and the valve operated to provide flow communication between the front and rear needles. By providing a rubberized valve with a frusto-conical section which closes off the passageway, an extremely simple and effective adapter can be produced.

What is claimed is:

1. A blood sampling device for obtaining arterial and venous blood samples, said sampling device being configured for use with an evacuated tube of the type having a stopper at one end which is designed to be pierced by a needle, said device comprising:

a hub member having a longitudinal conduit, a normally closed valve located in the middle of the conduit for preventing blood flow therethrough, wherein the valve is made of a one piece resilient material, said alve being generally perpendicular to and passing through the conduit, said valve including a lower frusto-conical portion which is normally biased against the conduit to prevent blood flow therethrough and an upper cylindrical portion extending to the outer surface of the hub member, whereby when pressure is applied to the upper portion, it will cause the lower portion to compress and move away from the contact with the conduit, thereby permitting blood to flow around the valve and through the conduit, said hub member further including a cylindrical tube receiving portion at one end;

a front needle extending from one end of the conduit, said front needle being configured for insertion into a blood vessel of a patient; and a rear needle extending from the other end of the conduit and into the tube receiving portion, whereby an evacuated tube can be inserted into the tube receiving portion and the stopper punctured by the rear needle prior to insertion of the front needle into a blood vessel without destroying the vacuum conditions of the tube.

2. A blood sampling device according to claim 1 wherein said valve includes an indentation on the bottom of the frusto-conical portion and the hub member includes a protrusion which extends into said indentation and biases the valve into a closed position.

3. A blood sampling device according to claim 2 wherein said valve is made of polyurethane.

4. A blood sampling device according to claim 2 wherein said indentation is substantially conical and said protrusion is substantially conical.

* * * * *